United States Patent [19]

Sato et al.

[11] Patent Number: 4,499,321
[45] Date of Patent: Feb. 12, 1985

[54] METHOD FOR SELECTIVE DEALKYLATION OF 1,4-DIALKYLBENZENE

[75] Inventors: Hiroshi Sato; Norio Ishii; Shyuzo Nakamura, all of Osaka, Japan

[73] Assignee: Sumitomo Chemical Company, Limited, Osaka, Japan

[21] Appl. No.: 612,219

[22] Filed: May 21, 1984

[30] Foreign Application Priority Data

May 20, 1983 [JP] Japan ................................. 58-89570

[51] Int. Cl.$^3$ .............................................. C07C 4/12
[52] U.S. Cl. .................................................... 585/486
[58] Field of Search ........................................ 585/486

[56] References Cited

U.S. PATENT DOCUMENTS 4,297,243 10/1981 Moorehead .......................... 585/486

Primary Examiner—Curtis R. Davis
Attorney, Agent, or Firm—Sughrue, Mion, Zinn, Macpeak and Seas

[57] ABSTRACT

A method for selective dealkylation of 1,4-dialkylbenzene comprising selectively dealkylating a 1,4-dialkylbenzene in a dialkylbenzene mixture using as a catalyst crystalline zeolite having a silica/alumina ratio of at least 12 and a constrained index of 1 to 12 which is modified with an oxide of a metal or mettaloid, said crystalline zeolite being one ion-exchanged with a lithium ion.

7 Claims, No Drawings

METHOD FOR SELECTIVE DEALKYLATION OF 1,4-DIALKYLBENZENE

FIELD OF THE INVENTION

The present invention relates to a method for shape-selectively dealkylating a 1,4-dialkylbenzene in a dialkylbenzene mixture using a specified zeolite catalyst, to thereby remove the 1,4-dialkylbenzene from the mixture or reducing its concentration of the mixture. More particularly, the present invention is intended to inhibit the side reaction (e.g., oligomerization, cracking, etc.) of an olefin produced by the above described dealkylation and to keep the percent recovery and purity of the liberated olefin at a high level, to thereby facilitate the re-use of the olefin and improve the economy of the dealkylation.

BACKGROUND OF THE INVENTION

Generally, dialkylbenzenes obtained by the dealkylation of benzenes are a mixture of 1,2-, 1,3- and 1,4-isomers, but a difference in boiling point between these isomers is so small that, in many cases, even rectifying columns having many plates are insufficient to separate these isomers from one another by distillation. Next, one specific example will be given. Cymene isomers obtained by the alkylation of toluene with propylene have the following boiling points: o-Isomer, 178.3° C.; m-isomer, 175.1° C.; and p-isomer, 177.1° C. A difference in boiling point between m- and p-cymenes, which comes into special question in the cresol manufacturing process, is only 2° C., so that separation of the both by rectification is extremely difficult. In the cresol manufacturing process now in use, therefore, the following procedure is employed: The mixed cymene, without being separated into the isomers, is oxidized as such into a mixed cresol (in this oxidation, the oxidation rate of o-cymene is very slow as compared with m- and p-cymenes so that the mixed cresol obtained consists mainly of m-cresol and p-cresol in general), and thereafter, separation of the cresol isomers is carried out.

As one method to separate the cresol isomers from one another, there is a one in which the cresol mixture is alkylated with isobutylene into a mixture of tert-butyl cresol isomers, the isomers are separated from one another by rectification taking advantage of a large difference in boiling point between them, and then the tertiary butyl group is eliminated to obtain high-purity m- and p-cresols.

As another method to separate the cresol isomers from one another, there is a one in which a mixture of cresol/urea isomeric clathrate compounds is separated into the isomers by recrystallization taking advantage of a difference in crystallizability between them, and the separated compounds are decomposed to obtain high-purity m- and p-cresols.

The foregoing both methods are a separation method now in use in industry, but their process is so complicated that a furthermore improvement is desired.

Another specific example will be given below. Diisopropylbenzene obtained by the alkylation of benzene, which is a starting material for 1,3-dihydroxybenzene (resorcinol) and 1,4-dihydroxybenzene (hydroquinone), comprises the isomers having the following boiling points: o-Isomer, 200° C.; m-isomer, 203.2° C.; and p-isomer, 210.3° C. A difference in boiling point between m- and p-diisopropylbenzenes, which comes into special question in the resorcinol and hydroquinone manufacturing process, is 7° C., so that separation of the both by rectification is possible. This method, however, requires rectifying columns having a fairly large number of plates so that it may not always be said to be a separation method of good efficiency.

Instead of these conventional separation methods, there are proposed ones based on a new idea which are intended to selectively dealkylate only the 1,4-dialkyl isomer in the dialkylbenzene, to thereby recover the 1,3-dialkyl isomer (in some cases, 1,2- plus 1,3-dialkyl isomers) as unreacted (Japanese Patent Application (OPI) Nos. 93716/1980 and 83721/1980). (The term "OPI" as used herein refers to a "published unexamined Japanese patent application", hereinafter the same). This method uses a ZSM type zeolite as a catalyst, and particularly, a ZSM type zeolite catalyst modified with oxides such as MgO, $P_2O_5$, etc. will dealkylate only the 1,4-dialkyl isomer with a very high selectivity, so that this method is a markedly epoch-making technique.

From the practical point of view, however, this method also has one large defect that, when the alkyl group to be dealkylated has not less than three carbon atoms, olefins obtained by the dealkylation are low in purity and percent recovery. For example, Example 10 of Japanese Patent Application (OPI) No. 83716/1980 discloses that m-cymene is obtained in a high purity (96.6%) by dealkylating a mixed cymene (o:m:P=2.16:66.16:31.67) using a steam-treated H-ZSM-5, but the content of recovered propylene in the volatile gas obtained at that time is about 60%. Similarly, Example 11 of Japanese Patent Application (OPI) No. 83721/1980 discloses that a high-purity m-cymene is obtained by dealkylating a mixed cymene using a similar catalyst, but the content of propylene recovered at that time is 43%. In the above two cases, the volatile gas contains $C_2$–$C_5$ hydrocarbons in addition to propylene. When an industrial process is taken into account, olefins produced by dealkylation (propylene in the case of dealkylation of cymene) need to be re-used by recycling to the alkylation zone, otherwise the material cost becomes too high to establish a practical industrial process. When the olefin purity is however low, the olefin is difficult to re-use as it is, and therefore separate olefin-purification equipments become necessary, which is a defect of this method.

On the other hand, Japanese Patent Application (OPI) No. 103119/1981 discloses that when the reaction is carried out in the presence of an H-ZSM-5 catalyst while feeding a mixed cymene and aniline or ammonia, the dealkylation proceeds with a high para-selectivity, whereby propylene is recovered in a high purity as 94%. Though this method is an excellent technique, it has the following defects: Namely, when an actual embodiment to be applied industrially is taken into account, while the recovered propylene is recycled into the alkylation region, if a base such as aniline or ammonia is entrained, the dealkylating catalyst becomes deactivated. Thus, it is necessary to separate aniline or ammonia and to purify propylene, which results in rendering the process not economical.

SUMMARY OF THE INVENTION

An object of the present invention is to provide a method for selectively dealkylating a 1,4-dialkylbenzene.

Another object of the present invention is to improve the purity of olefins recovered after the dealkylation.

A further object of the present invention is to obtain a 1,3-dialkylbenzene (m-isomer) in a state that the purity thereof is high or the proportion thereof is dominant, from a mixed dialkylbenzene.

Still a further object of the present invention is to obtain dialkylbenzenes such as m-cresol or resorcinol in a state that the purity thereof is high or the proportion thereof is dominant.

DETAILED DESCRIPTION OF THE INVENTION

First, the present inventors began with making a follow-up test on the prior arts, i.e., aforementioned Japanese Patent Application (OPI) Nos. 83716/1980 and 83721/1980.

From the test results shown in the comparative experiments, it was confirmed that, when the mixed cymene was dealkylated using as a catalyst ZSM type zeolite (e.g., ZSM-5) modified with the oxide of a metal or metalloid (e.g., MgO), only p-cymene was dealkylated with a high selectivity, but at the same time, it became also clear that the purity and percent recovery of the recovered propylene were extremely low. The volatile gas obtained at that time contains many kinds of $C_2$–$C_6$ olefins and paraffins in addition to propylene, from which it is supposed that the liberated isopropyl group was subjected to complicated side reactions such as oligomerization, cracking, hydrogenation, etc. Also, the total carbon content of the $C_2$–$C_6$ volatile gases is lower than that of the liberated isopropyl groups, from which it is supposed that some parts of the volatile gases were changed to heavy components having more than six carbon atoms.

In order to achieve these objects, the present inventors extensively studied and found a surprising fact that both maintenance of the dealkylation activity and inhibition of the side reaction can be attained simultaneously by ion-exchanging an H type crystalline zeolite with a lithium ion. The present inventors thus attained to the present invention. Further, in this case, by using the zeolite modified with the oxide of a metal or metalloid, the 1,4-isomer alone in a dialkylbenzene can selectively be dealkylated.

According to the present invention, there is provided the following method: In a method wherein a 1,4-dialkylbenzene in a dialkylbenzene mixture is selectively dealkylated using as a catalyst crystalline zeolite, its silica/alumina ratio being at least 12 and constrained index being 1 to 12, modified with the oxide of a metal or metalloid, a method for the selective dealkylation of 1,4-dialkylbenzene is characterized by using crystalline zeolite ion-exchanged with a lithium ion.

In the present invention, the dialkylbenzene to which the gist of the present invention can apply particularly advantageously is compounds containing a secondary and/or tertiary alkyl group having 3 to 12 carbon atoms. Specific examples of the 1,4-dialkylbenzene include, for example, 1-isopropyl-4-methylbenzene, 1,4-diisopropylbenzene, 1-sec-butyl-4-methylbenzene, 1-tert-butyl-4-methylbenzene, and the like. The effect of the present invention consists in two points: The first point is that the 1,4-dialkylbenzene alone contained in the dialkylbenzene mixture can selectively be dealkylated; and the second point is that the formed olefin (e.g., propylene for 1-isopropyl-4-methylbenzene; isobutylene for 1-tert-butyl-4-methylbenzene) can be recovered in a high yield and high purity.

Consequently, by incorporating the method of the present invention after the usual alkylation, the m-dialkyl isomer (or m- and o-dialkyl isomers) can be obtained in a high purity, and besides benzenes and olefins produced by dealkylation can be recycled as such to the alkylation step. This method, therefore, becomes a very rational process. Depending upon the object, this method may be used in such a manner as to regulate the isomer distribution only by limiting the percent dealkylation of the p-isomer to a specified range.

Next, the method of the present invention will be illustrated specifically. The crystalline aluminosilicate zeolite catalyst used in the present invention (hereinafter referred to as zeolite catalyst) is a novel zeolite having characteristics that the silica/alumina molar ratio is 12 or more and besides the constrained index (described later) is 1 to 12, and its typical example is those (pentacyl type zeolites) which were developed by Mobile Oil Co. in relatively recent years and are generically called "ZSM type zeolite".

The characteristic of ZSM type zeolite is a high silica/alumina molar ratio, and this molar ratio can be measured by the common analytical methods such as atomic absorption method. This molar ratio expresses a value as near to the molar ratio in the skeleton of zeolite crystals as possible, with the exception of aluminum contained in the binder, cations in the channel and other forms. An effective zeolite is a one having a silica/alumina molar ratio of at least 12, but in some cases, zeolite having silica/alumina molar ratios as very high as, for example, 500 is also effective.

The constrained index used in the present invention is defined by the following equation:

$$\text{Constrained index} = \frac{\log_{10} (\text{content of remaining hexane})}{\log_{10} (\text{content of remaining 3-methylpentane})}$$

This index was originally thought out by the research workers of Mobile Oil Co., and it means a degree to which the channel of the zeolite crystal controls the access to itself of molecules having a section larger than that of n-paraffin. The specific measurement method is described in Japanese Patent Application (OPI) No. 133223/1981.

The value of this constrained index approaches the ratio of cracking rates of the both hydrocarbons.

A preferred zeolite of the present invention is a one having a constrained index of 1 to 12. The constrained index of some typical zeolite is shown below:

|        | Constrained index |        | Constrained index |
|--------|-------------------|--------|-------------------|
| ZSM-5  | 8.3               | ZSM-35 | 4.5               |
| ZSM-11 | 8.7               | ZSM-38 | 2                 |
| ZSM-12 | 2                 | ZSM-48 | 3.4               |
| ZSM-23 | 9.1               |        |                   |

These are disclosed in detail in Japanese Patent Publication No. 10064/1971, and their preparation method and X-ray diffraction pattern described therein are incorporated herein by reference.

In the present invention, the aforementioned value of the constrained index is the important critical definition of a useful zeolite. Since, however, some latitude is allowed in the measurement method described above, the value sometimes varies with the measurement condition.

Consequently, the value of the constrained index is a mean value of those obtained under some different measurement conditions.

As shown above, the crystalline zeolite used in the method of the present invention was defined by means of two values, one being a silica/alumina molar ratio and the other being a constrained index. Specific examples of said zeolite include a series of ZSM type zeolite developed by Mobile Oil Co., i.e. ZSM-5, ZSM-11, ZSM-12, ZSM-23, ZSM-35, ZSM-38 and ZSM-48.

Next, reference will be made to the lithium ion-exchange which is most important in the method of the present invention.

ZSM type zeolite is generally hydrothermally synthesized in the coexistence of an organic cation and a sodium ion. Next, using ZSM type zeolite freshly synthesized as a starting material, the procedures of activation and ion-exchange will be illustrated with reference to ZSM-5.

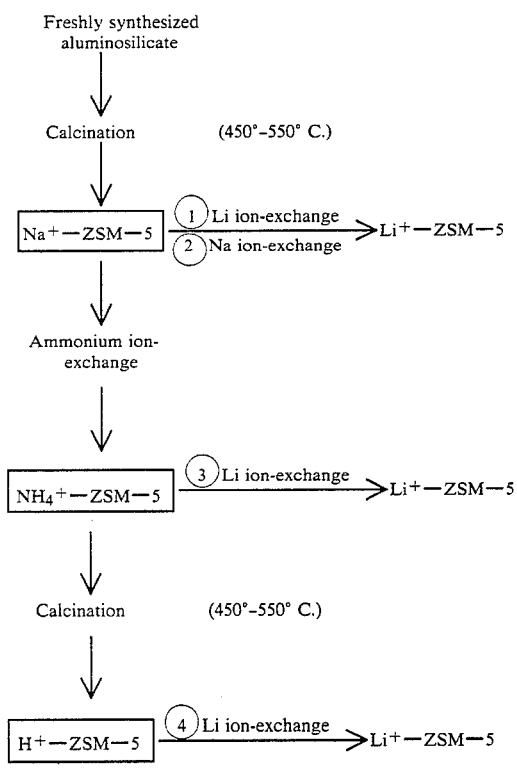

There are three stages to which lithium ion-exchange can be applied, i.e., ① Na+-ZSM-5, ③ NH4+-ZSM-5 and ④ H+-ZSM-5, and they are not particularly limited. But, lithium ion-exchange of ① Na+-ZSM-5 or ③ NH4+-ZSM-5 is better in terms of efficiency. Alternatively, since there may be a case that the calcined Na+-ZSM-5 contains an H+ cation generated after the calcination of the organic amine cation, a good catalytic property may be obtained by lithium ion-exchange of ② Na+-ZSM-5 again subjected to sodium ion-exchange which is a complete Na type.

The procedure of lithium ion-exchange may be carried out as usual. For example, referring to the case of ZSM-5 described above, one of ① Na+-ZSM-5, ② Na+-ZSM-5, ③ NH4+-ZSM-5 and ④ H+-ZSM-5 is dipped in an aqueous solution containing an Li+ ion source, and it is thoroughly ion-exchanged with an Li+ ion by repeating an ion-exchange/filtration cycle at a pre-determined temperature with stirring. As well known, an Li+ ion is hydrated with many water molecules although its ionic radius itself is small, and therefore, the hydrated Li+ ion has a relatively large radius, being one of the ions which are difficult to ion-exchange. In the ion-exchange operation, therefore, various devices are required so as to increase the rate of ion-exchange, for example, by keeping not only the Li+ ion source concentration but also the temperature a little high. Generally, temperatures of 80° to 100° C. will suffice. As the lithium ion source, lithium acetate, lithium hydroxide, lithium nitrate, lithium chloride, lithium bicarbonate, lithium carbonate, lithium phosphate, etc. are used.

These lithium compounds may be used alone or in admixture. Specially, in order to increase a degree of lithium ion-exchange, it is preferred to use a combination of lithium hydroxide with other Li+ salt. In this case, since in a too much high pH region, the elution of zeolite crystal occurs, such a pH region should be avoided.

A sufficiently high rate of lithium ion-exchange is required. For example, when ① Na+-ZSM-5 or ② Na+-ZSM-5 is a starting material, unexchanged Na+ ion sites turn inactive site, while when ③ NH4+-ZSM-5 or ④ H+-ZSM-5 is a starting material, unexchanged NH4+ ion sites or H+ ion sites act as a strong acid site to promote the side reactions of C3 or higher olefins produced by dealkylation such as oligomerization, hydrogen shift and the like. As a result, the gist of the present invention is damaged. The rate of lithium ion-exchange can be measured by means of the chemical elemental analysis (e.g., atomic absorption analysis).

Next, reference will be made to a method for the modification of ZSM type zeolite with the oxide of a metal or metalloid, which is applied in combination with the lithium ion-exchange in the method of the present invention. This method is modification of ZSM type zeolite with the oxide of a metal or metalloid by after dipping ZSM type zeolite in a solution containing a metal or metalloid compound and then concentration (in some cases, filtration is also included), or kneading ZSM type zeolite with a metal or metalloid compound in a dry or wet manner, calcining the zeolite at a temperature of 400° to 600° C. in an air stream. By this modification, the ZSM type zeolite is poisoned at the acid sites on the surface outside its channels, and the entrance of the channels is narrowed to some degree. Because of these two effects, it may be considered that the acid sites alone inside the channels work effectively to develop the so-called shape-selectivity (in other words, the p-isomer alone of dialkylbenzenes is selectively dealkylated).

This modification may be applied before or after the foregoing lithium ion-exchange. But, when this modification is to be carried out after lithium ion-exchange, quick treatment is required not to cause the re-exchange of Li+ ions.

The specific means of the modification are shown in the example described later, and the procedure used therein is as follows: NH4+-ZSM-5 is dipped in an aqueous lithium acetate solution, and an ion-exchange/filtration cycle is repeated four times at 90° C. to obtain Li-ZSM-5; this Li-ZSM-5 is impregnated with an aqueous magnesium acetate solution, and after concentration, calcined at 500° C. for 3 hours in an air stream to obtain MgO-modified Li-ZSM-5. This procedure is one example of many combinations of order.

The modification method with a metal or metalloid oxide used in the present invention is well known, and it includes for example the method of the present inventors' patent application (Japanese Patent Application (OPI) No. 159430/1983), the method of Mobile Oil Co. (Japanese Patent Application (OPI) Nos. 133030/1981, 133031/1981, 133032/1981, 133223/1981, 144750/1981, 145227/1981 and 10337/1982) and the like. The method of the present invention is characterized in that this well-known modification method is used in combination with the lithium ion-exchange method.

The metal or metalloid compound for modifying ZSM type zeolite is a compound of at least one element selected from the group consisting of the lanthanum elements (e.g., La, Ce, and Nd), the Group IIa elements (Ba, Mg, and Sr), the Group IIb elements (e.g., Zn and Cd), the Group IIIa elements (e.g., Ga and In), the Group IVa elements (e.g., Ge, Sn, and Pb), the Group Va elements (e.g., P), the Group VIa elements (e.g., Te), the Group VIb elements (e.g., Cr, Mo, and W), and the Group VIIb elements (e.g., Mn and Re).

This metal compound or metalloid compound is mixed with ZSM type zeolite in the form of a solution, and through the steps of concentration and calcination, it finally modifies the ZSM type zeolite catalyst in the form of, substantially, a metal oxide or metalloid oxide. Examples of a suitable solvent used in this case include for example water, aromatic or aliphatic hydrocarbons, alcohols, organic acids (e.g. formic acid, acetic acid, propionic acid) and inorganic acids (e.g. hydrochloric acid, nitric acid, sulfuric acid). Alternatively, halogenated hydrocarbons, ketones, ethers, etc. also are useful. Of these solvents, water is used most popularly. ZSM type zeolite is impregnated with this solution, and after concentration, it is dried, but in some cases, it is filtered after impregnation and dried. Drying is carried out at a temperature of generally 80° to 150° C. Calcination after drying is carried out at a temperature of not less than 300° C., preferably 400° to 550° C. for several hours in an air stream. The amount of the metal oxide or metalloid oxide modifying ZSM type zeolite after calcination is selected from a range of 1 wt% to 50 wt%.

The selective dealkylation of the 1,4-dialkyl isomer contained in a dialkylbenzene mixture is carried out by bringing the mixture into contact with the aforementioned metal or metalloid oxide-modified Li-ZSM type zeolite catalyst.

The dealkylation is mainly carried out by the gaseous-phase catalytic reaction.

The catalytic system of the present invention may be used alone but it is usually put into practical uses after diluting with a binder such as alumina and then pressure molding.

In this reaction, inert gases such as nitrogen, helium, argon, etc. may be used as a diluent. The use of diluent may be employed for the purpose of positively aiming to control the occurrence of side reactions by the action of the dilution of the substrate, to thereby keep the purity of the recovered olefin high, if any.

The reaction temperature cannot be determined simply because it is affected by the kind of alkyl groups to be dealkylated, but generally it is selected from a range of 250° to 600° C. The alkyl group which is an object of dealkylation of the present invention is a secondary and/or tertiary alkyl group having 3 to 12 carbon atoms. Generally, however, the progress of the dealkylation becomes easy as an increase in the number of carbon atoms of the alkyl group, or it is easier in tertiary alkyl groups than in secondary ones. The reaction temperature, therefore, shifts to a low temperature side.

One characteristic of the present catalytic system is that, if the dealkylation is carried out at high temperatures in order to raise its conversion, selectivity to the dealkylation of the 1,4-isomer is kept high (in other words, both the 1,2- and 1,3-isomers are left completely or nearly unreacted) and besides both the purity and percent recovery of the recovered olefin are also kept high.

For example, in case of a mixed cymene, superior reaction results are given as follows: Even if the conversion of p-cymene is high as 90% or more, not only the percent recovery of m-cymene, the yield of toluene, and the yield of propylene all become 90% or more but also the purity of propylene in the volatile fraction becomes 90% or more.

The contact time is selected from a range of 0.1 to 60 seconds, preferably 1 to 30 seconds.

Another characteristic of the present catalytic system is that, if the dealkylation is carried out for a long contact time in order to raise its conversion, selectivity to the dealkylation of the 1,4-isomer as well as the yield and purity of the recovered olefin are kept high.

A further characteristic of the present catalytic system is that, since the catalytic system has a long life, a reduction in the catalytic activity due to deposition of carbonaceous substances is very little even in the prolonged reaction.

The dealkylation of the present invention is carried out using a fixed-bed or fluidized-bed catalytic system according to a batchwise, semi-continuous or continuous process. In either case, for the regeneration of the catalyst, carbonaceous substances on the catalyst are burned out at a temperature of about 500° to about 550° C. using an inert gas containing a little oxygen (0.5 to 2.0%).

The present invention will be illustrated in more detail with reference to the following specific examples, but it is not to be interpreted as being limited thereto.

The reaction results in the examples were calculated by means of the following equations.

$$\text{Total conversion (\%)} = 1 - \frac{\text{unreacted dialkylbenzene (mole)}}{\text{starting dialkylbenzene (mole)}} \times 100$$

$$\text{Conversion of p-isomer (\%)} = 1 - \frac{\text{unreacted p-dialkylbenzene (mole)}}{\text{starting p-dialkylbenzene (mole)}} \times 100$$

$$\text{Yield of monoalkylbenzene (\%)} = \frac{\text{formed monoalkylbenzene (mole)}}{\text{starting dialkylbenzene (mole)}} \times 100$$

$$\text{Yield of olefin (\%)}^{(1)} = \frac{\text{formed olefin}^{(1)} \text{ (mole)}}{\text{starting dialkylbenzene (mole)}} \times 100$$

$$\text{Percent recovery of m-isomer (\%)} = \frac{\text{unreacted m-dialkylbenzne (mole)}}{\text{starting m-dialkylbenzene (mole)}} \times 100$$

$$\text{Percent recovery of o-isomer (\%)} = \frac{\text{unreacted o-dialkylbenzene (mole)}}{\text{starting o-dialkylbenzene (mole)}} \times 100$$

$$\text{Percent recovery of aromatic substance (\%)} = \frac{\text{recovered alkylbenzenes (mole)}}{\text{starting dialkylbenzene (mole)}} \times 100$$

-continued $$\text{Percent recovery of gas (\%)} = \frac{\text{recovered gas}^{(2)} \text{ (carbon, g-atom)}}{\text{liberated alkyl group (carbon, g-atom)}} \times 100$$

$$\text{Purity of olefin (\%)}^{(1)} = \frac{\text{formed olefin}^{(1)} \text{ (mole)}}{\text{recovered gas}^{(2)} \text{ (mole)}} \times 100$$

(1)An objective main olefin formed by dealkylation (e.g. propylene for cymene and isobutylene for tert-butyltoluene).
(2)Total $C_1$-$C_6$ volatile olefins and paraffins.

The analysis of the reaction products was carried out by gas chromatography.

REFERENCE EXAMPLE 1

Synthesis of ZSM-5

ZSM-5 was synthesized as follows based on British Pat. No. 1,402,981. 326 Grams of distilled water, 61 g of aluminum sulfate, 72 g of sodium chloride, 24 g of tetra-n-propylammonium bromide and 16 g of sulfuric acid were mixed in this order, and this solution was taken as A liquor. Thereafter, 239 g of water and 191 g of No. 3 sodium silicate were mixed, and this solution was taken as B liquor.

A and B liquors were added to a 1-liter stainless steel autoclave and mixed. A white gel was formed immediately, but stirring was continued. The autoclave was closed tightly, and hydrothermal synthesis was carried out by raising the temperature to 160° C. and continuing stirring (at 350 to 400 rpm) at this temperature. The gauge pressure showed 5 to 6 kg/cm². After 21 hours' reaction, the contents were taken out and filtered. After repeating five times a cycle of washing with 400 g distilled water/filtration, the reaction product was dried at 120° C. for 15 hours and then calcined at 540° C. for 4 hours while passing air at a rate of 10 ml/min. The amount of the white crystal obtained was 46 g, which corresponds to a yield of 82.6%. By X-ray diffraction measurement, it was found that the X-ray diffraction pattern of this white crystal agreed with that of ZSM-5 described in Japanese Patent Publication No. 10064/1971.

Thereafter, the Na-ZSM-5 obtained above was ion-exchanged by repeating a 65° C.×2 hours' ion-exchange three times using 200 g of a 5% aqueous ammonium chloride solution every time and then applying a 25° C.×overnight' ion-exchange using 200 g of the same aqueous solution, and then filtered. After repeating a cycle of washing with 200 g distilled water/filtration five times, the product was dried at 120° C. for 10 hours to obtain 37 g of $NH_4^+$-ZSM-5 crystals. Percent recovery was 81%. As a result of the atomic absorption analysis, it was found that the $SiO_2/Al_2O_3$ molar ratio of this crystal was 52.

REFERENCE EXAMPLE 2

Synthesis of ZSM-5

ZSM-5 was synthesized as follows based on Japanese Patent Application (OPI) No. 149900/1976.

48.5 Grams of pyrrolidine was added to a mixture of 74.9 g of distilled water and 10.1 g of sodium aluminate (NA-170, a product of Sumitomo Aluminum Co.; alumina content, 17.3 wt%), and then 439.3 g of a colloidal silica (Cataloid-SI-30, a product of Shokubai Kasei Co.; silica content, 30-31 wt%) was added. The mixture was vigorously stirred for 15 minutes. This mixed liquor was added to a 1-liter stainless steel autoclave, and crystallized while stirring (350-400 rpm) at 175° C. for 48 hours. After cooling, the reaction product was filtered, thoroughly washed with a large quantity of distilled water (about 10 liters) and filtered. After repeating this washing/filtration cycle, the product was dried at 115° C. to 120° C. for 15 hours in a nitrogen stream.

Thereafter, the product was calcined at 530° C. for 8 hours in an air stream to obtain 125 g of a white crystal. By the X-ray diffraction measurement, it was found that the X-ray diffraction pattern of this crystal agreed with that of ZSM-5 described in Japanese Patent Publication No. 10064/1971. The analysis by the atomic absorptiometric method showed that this product had an $SiO_2/Al_2O_3$ molar ratio of 107.4.

In the same manner as in the latter half of Reference Example 1, the product was ion-exchanged with an aqueous ammonium chloride solution and then dried at 120° C. for 10 hours to obtain $NH_4^+$-ZSM-5 crystals.

EXAMPLE 1-1

Synthesis of MgO-modified $Li^+$-ZSM-5

A MgO-modified $Li^+$-ZSM-5 was synthesized as follows using $NH_4^+$-ZSM-5 obtained in Reference Example 2. A mixture of 15 g of $NH_4^+$-ZSM-5 and 160 ml of a 3.5 wt% aqueous lithium acetate solution was heated with stirring at 90° C. for 30 minutes, and the product was filtered and washed with 100 ml of distilled water. After repeating this operation five times, the product was washed with five 500-ml portions of distilled water and dried at 100° C. for 2 hours.

Thereafter, to 11 g of the $Li^+$-ZSM-5 catalyst thus obtained was added 180 ml of an 8 wt% aqueous magnesium acetate solution, and the mixture was stirred and concentrated to dryness at 80° C. under reduced pressure. Thereafter, the product obtained was dried at 120° C. for one day and calcined at 500° C. for 2 hours in an air stream.

By the operation described above, 13 g of MgO-modified $Li^+$-ZAM-5 (amount of supporting MgO: 20 wt%) was obtained as a grayish white crystal.

EXAMPLE 1-2:

Catalytic activity test by fixed-bed flow reaction

Dealkylation of cymene was carried out as follows using the common normal-pressure fixed-bed flow reactor.

A quartz glass tubular reactor, 32 cm in length and 1 cm in inside diameter, was packed with 1 g of the 20 wt% MgO-modified $Li^+$-ZSM-5 catalyst (24–48 mesh) synthesized in Example 1-1, and the catalyst was preheated at 400° C. for 1 hour in a nitrogen stream. Thereafter, a mixed cymene (m:p:o=63.6:32.9:3.5) and a nitrogen gas were fed to the reactor at a WHSV (weight hourly space velocity) of 4.6 hr$^{-1}$ and at a rate of 1200 ml/hr, respectively, to carry out the dilution and reaction of the mixed cymene. The temperature of the catalyst bed was stepwise changed from 350° C. to 400° C. The contact time was about 4.5 seconds. The reaction product was collected by trapping with ice-cooling, and the aromatic component was analyzed by gas chromatography. The volatile gas component was analyzed in situ by introducing the mixed reaction gas directly into a gas chromatograph.

The result obtained is shown in Table 1.

EXAMPLE 2

Dealkylation of cymene was carried out according to Example 1-2 using 2 g of the same 20 wt% MgO-modified Li+-ZSM-5 catalyst as used in Example 1.

A mixed cymene (m:p:o=63.6:32.9:3.5) was fed at a WHSV of 2.3 hr$^{-1}$, a nitrogen gas was fed at a rate of 2600 ml/hr, and the contact time was about 9.2 seconds. The reaction temperature was stepwise changed from 350° C. to 400° C., 450° C. and then 500° C. The results of stationary activity test at every temperature are shown in Table 2.

The reaction temperature was 500° C., and both the SV (space velocity) of cymene (m:p:o=63.6:32.9:3.5) and the contact time were changed stepwise.

The results of stationary activity test for every contact time are shown in Table 3.

EXAMPLE 4

Dealkylation of cymene was carried out according to Example 1-2 using 2 g of the same 20 wt% MgO-modified Li+-ZSM-5 catalyst as used in Example 1.

The reaction temperature was 500° C., the WHSV of cymene (m:p:o=63.6:32.9:3.5) was 0.93 hr$^{-1}$, the flow rate of nitrogen gas was 462 ml/hr, and the contact time was 21.9 seconds.

Fifty hours after beginning of the reaction, sampling was carried out seven times each one hour while continuing the reaction, and the samples collected were analyzed. The results are shown in Table 4.

TABLE 1

| Run No. | Reaction temperature (°C.) | Conversion (%) p-Cymene | Conversion (%) Total cymene | Yield (%) Toluene | Yield (%) Propylene | Percent recovery (%) m-Cymene | Percent recovery (%) o-Cymene | Percent recovery (%) Total aromatic substance | Gas component | Purity of propylene (%) | Composition of gas component* (mole %) $C'_2$ | $C'_3$ | $C_3$ | $C'_4$ | $C'_5$ | $C'_6$ |
|---|---|---|---|---|---|---|---|---|---|---|---|---|---|---|---|---|
| 1 | 350 | 18.7 | 7.9 | 4.9 | 5.5 | 97.4 | 97.4 | 97.0 | 77.0 | 94 | 0 | 94 | 0 | 0 | 6 | 0 |
| 2 | 400 | 53.4 | 17.9 | 13.9 | 16.3 | 96.2 | 94.1 | 96.0 | 92.0 | 99 | 0 | 99 | 0 | 1 | 0 | 0 |
| 3 | 450 | 67.4 | 25.2 | 20.7 | 22.6 | 95.5 | 96.6 | 98.0 | 94.0 | 95 | 3 | 95 | 0 | 0.8 | 1.2 | 0.8 |

*$C'_n$ denotes "olefin" and $C_n$ denotes "paraffin" (hereinafter the same).

TABLE 2

| Run No. | Reaction temperature (°C.) | Conversion (%) p-Cymene | Conversion (%) Total cymene | Yield (%) Toluene | Yield (%) Propylene | Percent recovery (%) m-Cymene | Percent recovery (%) o-Cymene | Percent recovery (%) Total aromatic substance | Gas component | Purity of propylene (%) | Composition of gas component* (mole %) $C'_2$ | $C'_3$ | $C_3$ | $C'_4$ | $C'_5$ | $C'_6$ |
|---|---|---|---|---|---|---|---|---|---|---|---|---|---|---|---|---|
| 1 | 350 | 25.4 | 8.7 | 8.2 | 8.2 | 99 | 100 | 100 | 100 | 96 | 0 | 96 | 0 | 0 | 4 | 0 |
| 2 | 400 | 60.9 | 23.6 | 18.6 | 20.8 | 94 | 99 | 95 | 88 | 94 | 0 | 94 | 0 | 0 | 6 | 0 |
| 3 | 450 | 82.4 | 30.9 | 25.9 | 28.3 | 94 | 95 | 95 | 100 | 94 | 0 | 94 | 0 | 0 | 1 | 5 |
| 4 | 500 | 88.4 | 31.1 | 29.7 | 28.1 | 97 | 99 | 99 | 100 | 94 | 0 | 94 | 0 | 3 | 2 | 1 |

EXAMPLE 3

Dealkylation of cymene was carried out according to Example 1-2 using 2 g of the same 20 wt% MgO-modified Li+-ZSM-5 catalyst as used in Example 1.

TABLE 3

| Run No. | Contact time (sec) | Conversion (%) p-Cymene | Conversion (%) Total cymene | Yield (%) Toluene | Yield (%) Propylene | Percent recovery (%) m-Cymene | Percent recovery (%) o-Cymene | Percent recovery (%) Total aromatic substance | Gas component | Purity of propylene (%) | Composition of gas component (mole %) $C'_2$ | $C'_3$ | $C_3$ | $C'_4$ | $C'_5$ | $C'_6$ |
|---|---|---|---|---|---|---|---|---|---|---|---|---|---|---|---|---|
| 1 | 4.0 | 68.6 | 23.6 | 21.6 | 22.6 | 98 | 100 | 98 | 100 | 97 | 3 | 97 | 0 | 0 | 0 | 0 |
| 2 | 5.8 | 80.1 | 28.4 | 24.2 | 25.2 | 97 | 99 | 96 | 100 | 92 | 0 | 92 | 0 | 2 | 5 | 1 |
| 3 | 8.1 | 87.7 | 31.0 | 26.8 | 30.0 | 97 | 100 | 96 | 100 | 98 | 0 | 98 | 0 | 0.5 | 0 | 1.5 |
| 4 | 10.2 | 91.2 | 32.9 | 28.2 | 29.0 | 95 | 100 | 96 | 100 | 93 | 1 | 93 | 0 | 0 | 0 | 5 |
| 5 | 14.9 | 94.3 | 34.6 | 29.6 | 32.5 | 95 | 98 | 95 | 100 | 96 | 1 | 96 | 0 | 1 | 0 | 2 |
| 6 | 21.9 | 100 | 34.9 | 31.7 | 32.5 | 97 | 95 | 97 | 100 | 96 | 0 | 96 | 0 | 2 | 0 | 2 |

TABLE 4

| Run No. | Total reaction time (hr) | Conversion (%) p-Cymene | Conversion (%) Total cymene | Yield (%) Toluene | Yield (%) Propylene | Percent recovery (%) m-Cymene | Percent recovery (%) o-Cymene | Percent recovery (%) Total aromatic substance | Gas component | Purity of propylene (%) | Composition of gas component (mole %) $C'_2$ | $C'_3$ | $C_3$ | $C'_4$ | $C'_5$ | $C'_6$ |
|---|---|---|---|---|---|---|---|---|---|---|---|---|---|---|---|---|
| 1 | 50 | 100 | 33.4 | 32.5 | 30.9 | 99 | 98 | 100 | 100 | 95 | 1 | 95 | 0 | 2 | 0 | 2 |
| 2 | 51 | 100 | 33.0 | 33.0 | 30.4 | 100 | 100 | 100 | 100 | 92 | 2 | 92 | 0 | 2 | 2 | 2 |
| 3 | 52 | 100 | 34.7 | 32.0 | 30.7 | 97 | 100 | 98 | 100 | 92 | 2 | 92 | 0 | 2 | 2 | 2 |
| 4 | 53 | 100 | 34.9 | 31.7 | 32.5 | 97 | 95 | 97 | 100 | 96 | 0 | 96 | 0 | 2 | 0 | 2 |
| 5 | 54 | 100 | 33.5 | 33.0 | 30.3 | 99 | 98 | 100 | 100 | 92 | 3 | 92 | 0 | 2 | 1 | 2 |

TABLE 4-continued

| Run No. | Total reaction time (hr) | Conversion (%) p-Cymene | Yield (%) Total cymene | Toluene | Propylene | Percent recovery (%) m-Cymene | o-Cymene | Total aromatic substance | Gas component | Purity of propylene (%) | Composition of gas component (mole %) $C'_2$ | $C'_3$ | $C_3$ | $C'_4$ | $C'_5$ | $C'_6$ |
|---|---|---|---|---|---|---|---|---|---|---|---|---|---|---|---|---|
| 6 | 56 | 100 | 32.5 | 32.4 | 30.2 | 100 | 99 | 100 | 100 | 95 | 1 | 95 | 0 | 2 | 0 | 2 |
| 7 | 58 | 100 | 34.9 | 31.1 | 32.1 | 97 | 95 | 97 | 100 | 95 | 0 | 95 | 0 | 2 | 1 | 2 |

COMPARATIVE EXAMPLE 1

$NH_4^+$-ZSM-5 synthesized in Reference Example 2 was calcined at 540° C. for 4 hours in an air stream to obtain $H^+$-ZSM-5. Using 1 g of this catalyst (24–48 mesh), dealkylation of cymene (m:p:o=63.6:32.9:3.5) was carried out according to Example 1-2. The WHSV of cymene was 5.27 $hr^{-1}$, the flow rate of diluent nitrogen gas was 704 ml/hr, and the contact time was about 4.2 seconds. The reaction result obtained at a reaction temperature of 250° C. is shown in Table 5.

COMPARATIVE EXAMPLE 2

$H^+$-ZSM-5 obtained in Comparative Example 1 was steam-treated at 600° C. for 1 hour according to Example 11 of Japanese Patent Application (OPI) No. 83721/1980. Using 1 g of this catalyst, dealkylation of cymene (m:p:o=63.6:32.9:3.5) was carried out according to Example 1-2. The WHSV of cymene was 4.92 $hr^{-1}$, the flow rate of diluent nitrogen gas was 820 ml/hr, and the contact time was about 4.2 seconds. The reaction result obtained at a reaction temperature of 250° C. is shown in Table 5.

COMPARATIVE EXAMPLE 3

1.5 Grams of the $NH_4^+$-ZSM-5 catalyst synthesized in Reference Example 2 was dipped in an aqueous solution containing 8.92 mole of magnesium acetate at room temperature for 20 minutes with stirring. The mixture was then concentrated under reduced pressure, and dried at 120° C. for 20 hours. Subsequently, the dried product was calcined at 500° C. for 3 hours in an air stream to obtain a 20 wt% MgO-modified $H^+$-ZSM-5. Using 1 g of this catalyst, dealkylation of cymene (m:p:o=63.6:32.9:3.5) was carried out according to Example 1-2. The WHSV of cymene was 4.61 $hr^{-1}$, the flow rate of diluent nitrogen gas was 1130 ml/hr, and the contact time was about 4.7 seconds. The reaction result obtained at a reaction temperature of 350° C. is shown in Table 5.

TABLE 5

| Comparative Example No. | Catalyst | Reaction temperature (°C.) | Conversion (%) p-Cymene | Total cymene | Yield (%) Toluene | Propylene |
|---|---|---|---|---|---|---|
| 1 | $H^+$-ZSM-5 | 250 | 54.3 | 19.2 | 18.8 | 0.7 |
| 2 | Steam-treated $H^+$-ZSM-5 | 250 | 39.0 | 15.9 | 14.2 | 1.6 |
| 3 | MgO-modified $H^+$-ZSM-5 | 350 | 98.3 | 37.4 | 31.0 | 3.5 |

| Comparative Example No. | Percent recovery (%) Total aromatic substance | | | | Purity of propylene (%) |
|---|---|---|---|---|---|
| ple No. | m-Cymene | o-Cymene | aromatic substance | Gas component | propylene (%) |
| 1 | 97.7 | 91.8 | 100 | 47.0 | 11 |
| 2 | 95.5 | 94.0 | 100 | 67.0 | 22 |
| 3 | 93.4 | 92.0 | 94 | 56.0 | 22 |

| Comparative Example No. | Composition of gas component (mole %) $C'_2$ | $C'_3$ | $C_3$ | $C'_4$ | $C'_5$ | $C'_6$ |
|---|---|---|---|---|---|---|
| 1 | 1 | 11 | 2 | 46 | 28 | 12 |
| 2 | 2 | 22 | 0 | 32 | 26 | 18 |
| 3 | 6 | 22 | 11 | 40 | 17 | 6 |

REFERENCE EXAMPLE 3

Synthesis of ZSM-5

The starting liquors of the following composition were first prepared:

| A liquor | | B liquor | |
|---|---|---|---|
| Water | 162 g | Water | 119.7 g |
| $H_2SO_4$ | 16.7 g | No. 3 Sodium silicate | 186.3 g |
| $Al_2(SO_4)_3 \cdot 17H_2O$ | 2.92 g | | |
| (n-Pr)$_4$NBr | 20.3 g | | |
| C liquor | | | |
| Water | 281.7 g | | |
| NaCl | 70.9 g | | |

The above liquors were mixed by the simultaneous dropping of A and B liquors to C liquor. At that time, the mixed liquor was vigorously stirred while keeping the pH of the system at 9 to 11 (for pH adjustment, 6.0 g of a 48% aqueous NaOH solution was added). The pH on completion of the mixing was 9.55. The mixture was added to a 1-liter SUS autoclave, and hydrothermal synthesis was carried out at 160° C. for 20 hours with stirring (N=350 to 400 rpm). After cooling, the reaction mixture was filtered, thoroughly washed with a large quantity of distilled water (up to 7 liters), and then filtered. This washing/filtration cycle was repeated. The reaction product was dried at 120° C. for 15 hours and calcined at 530° C. for 3 hours in an air stream to obtain 47.6 g of a white powdery crystal. As a result of X-ray diffraction measurement, this product was identified to be ZSM-5.

The $SiO_2/Al_2O_3$ molar ratio was 84.

Next, in the same manner as in the latter half of Reference Example 1, this product was ion-exchanged with an aqueous ammonium chloride solution and dried at 120° C. for 10 hours to obtain $NH_4^+$-ZSM-5.

EXAMPLE 5-1

Using $NH_4^+$-ZSM-5 obtained in Reference Example 3, Li ion-exchange, Mg(OAc)$_2$ impregnation/support and calcination were applied according to Example 1-1 to prepare a 20 wt% MgO-modified Li+-ZSM-5 catalyst.

EXAMPLE 5-2

Using the MgO-modified Li+-ZSM-5 catalyst prepared in Example 5-1, the activity test was carried out according to Example 1-2, provided that the reaction condition was as follows: No dilution with nitrogen and SV=200 hr$^{-1}$. The result obtained is shown in Table 6.

TABLE 6

| Run No. | Reaction temperature (°C.) | Conversion (%) | | Yield (%) | | Percent recovery of m-cymene (%) | Purity of propylene (%) |
|---|---|---|---|---|---|---|---|
| | | p-Cymene | Total cymene | Toluene | Propylene | | |
| 1 | 350 | 33.2 | 14.5 | 13.5 | 13.0 | 98.9 | 100 |
| 2 | 450 | 82.8 | 30.2 | 29.0 | 27.3 | 96.5 | 98.3 |

EXAMPLE 6

Using the MgO-modified Li+-ZSM-5 catalyst prepared in Example 5-1, a prolonged reaction was carried out to examine the life of the catalyst according to Example 1-2, provided that the reaction condition was as follows: No dilution with nitrogen, SV=200 hr$^{-1}$ and reaction temperature=450° C. The result obtained is shown in Table 7.

TABLE 7

| Time elapsed (hrs) | Conversion (%) | | Yield (%) | | Percent recovery of m-cymene (%) | Purity of propylene (%) |
|---|---|---|---|---|---|---|
| | p-cymene | Total cymene | Toluene | Propylene | | |
| 10 | 86.5 | 32.2 | 31.5 | 30.2 | 96.8 | 95.9 |
| 63 | 87.6 | 31.7 | 30.4 | 28.0 | 98.3 | 95.5 |
| 100 | 86.7 | 31.7 | 31.0 | 29.2 | 97.6 | 95.0 |
| 163 | 86.5 | 33.7 | 31.2 | 30.6 | 94.2 | 95.4 |
| 193 | 86.3 | 33.4 | 30.7 | 29.0 | 94.7 | 95.5 |
| 257 | 85.1 | 33.6 | 31.0 | 29.5 | 95.6 | 95.4 |
| 311 | 84.0 | 32.4 | 30.5 | 28.7 | 94.9 | 96.2 |
| 354 | 83.0 | 31.2 | 29.0 | 29.5 | 96.3 | 95.7 |
| 412 | 80.4 | 29.7 | 29.0 | 28.5 | 97.0 | 96.0 |
| 477 | 78.8 | 39.9 | 29.0 | 27.0 | 94.4 | 96.0 |
| 528 | 80.1 | 31.2 | 28.5 | 26.2 | 94.8 | 97.0 |

REFERENCE EXAMPLE 4

Synthesis of ZSM-5

ZSM-5 was synthesized in the same manner as in Reference Example 3 except that the amount of Al$_2$(SO$_4$)$_3$.17H$_2$O was changed to 2.34 g and the number of agitations on the hydrothermal synthesis was changed to 120 rpm. The SiO$_2$/Al$_2$O$_3$ molar ratio of the resulting ZSM-5 crystal was 83.8. This product was washed, dried and calcined at 530° C. for 3 hours in an air stream in the same manner as in Reference Example 3. Thereafter, Na iron-reexchange was carried out according to the following procedure: Five grams of the calcined ZSM-5 was dispersed in a mixed solution of 100 ml of a 0.1M/L NaCl aqueous solution and 50 ml of a 0.1M/L NaOH aqueous solution, stirred at room temperature for 1 hour and then filtered; after repeating the same ion-exchange operation once more, the product was thoroughly washed, filtered and then dried at 120° C. for 10 hours to obtain Na+ ion-reexchanged type Na+-ZSM-5.

EXAMPLE 7-1

Preparation of MgO-modified Li+-ZSM-5

Using Na+-ZSM-5 synthesized in Reference Example 4, NH$_4$+ ion-exchange, Li+ ion-exchange, Mg(OAc)$_2$ impregnation/support and then calcination were applied according to Example 1-1 to prepare a 20 wt% MgO-modified Li+-ZSM-5 catalyst.

EXAMPLE 7-2

Using the MgO-modified Li+-ZSM-5 catalyst prepared in Example 7-1, the catalytic activity test was carried out according to Example 1-2, provided that the reaction condition was as follows: No dilution with nitrogen, SV=200 hr$^{-1}$ and reaction temperature=450° C. The result obtained is shown in Table 8.

TABLE 8

| Example No. | p-Cymene | Total cymene | Toluene | Propylene | Percent Recovery of m-cymene (%) | Purity of propylene (%) |
|---|---|---|---|---|---|---|
| Example 7-2 | 69.4 | 24.9 | 23.7 | 23.5 | 98.7 | 97.6 |
| Example 8-2 | 43.7 | 17.7 | 16.5 | 16.3 | 95.9 | 96.3 |

REFERENCE EXAMPLE 5

Synthesis of ZSM-5

ZSM-5 was synthesized in the same manner as in Reference Example 3 except that the amount of Al$_2$(SO$_4$)$_3$.17H$_2$O was changed to 11.68 g, provided that, just before shifting to the hydrothermal synthesis, the pH of the mixed liquor was adjusted to 9.50 with addition of an aqueous NaOH solution. The pH just after the hydrothermal synthesis was 12.3. In the same manner as in Reference Example 3, washing with water, drying and then calcination were applied to obtain a white ZSM-5 crystal. The SiO$_2$/Al$_2$O$_3$ molar ratio of the crystal was 34.6.

EXAMPLE 8-1

Five grams of the calcined ZSM-5 obtained in Reference Example 5 was dispersed in a mixed solution of 100 ml of a 0.1M/L NaCl aqueous solution and 50 ml of a 0.1M/L NaOH aqueous solution, stirred at room temperature for 1 hour and then filtered; after repeating the same ion-exchange operation once more, the product was thoroughly washed, filtered and then dried at 120° C. for 10 hours to obtain Na+ ion-reexchanged type Na+-ZSM-5.

Using this product, ion-exchange and impregnation/support treatment were carried out as follows: Five grams of Na+-ZSM-5 was dispersed in a mixed solution of 100 ml of a 0.1M/L LiNO$_3$ aqueous solution and 50 ml of a 0.1M/L LiOH aqueous solution, stirred for 1 hour under reflux and then filtered; after repeating the same ion-exchange operation once more, the product was thoroughly washed, filtered and then dried at 120° C. for 5 hours to obtain Li+-ZSM-5. According to Example 1-1, this product was subjected to Mg(OAc)$_2$ impregnation/support and 530° C.×3 hours' calcination in air to obtain a 20 wt% MgO-modified Li+-ZSM-5 catalyst.

EXAMPLE 8-2

Using the MgO-modified Li+-ZSM-5 catalyst prepared in Example 8-1, the catalytic activity test was carried out according to Example 1-2, provided that the reaction condition was as follows: No dilution with nitrogen, SV=200 hr$^{-1}$ and reaction temperature=450° C. The result obtained is shown in Table 8.

EXAMPLE 9-1

Five grams of the calcined ZSM-5 obtained in Reference Example 5 was dispersed in a mixed solution of 100 ml of a 0.2M/L LiCl aqueous solution and 50 ml of a 0.2M/L LiOH aqueous solution, stirred for 1 hour under reflux and then filtered; after repeating the same ion-exchange operation once more, the product was thoroughly washed, filtered and then dried at 120° C. for 10 hours to obtain Li+-ZSM-5. According to Example 1-1, this product was subjected to Mg(OAc)$_2$ impregnation/support and 530° C.×3 hours' calcination in air to obtain a 20 wt% MgO-modified Li+-ZSM-5 catalyst.

EXAMPLE 9-2

Using the MgO-modified Li+-ZSM-5 catalyst prepared in Example 9-1, the catalytic activity test was carried out according to Example 1-2. The reaction temperature was 450° C., and other reaction conditions are shown in Table 9 together with the result obtained.

ml of a 0.1M/L LiNO$_3$ aqueous solution and 50 ml of a 0.1M/L LiOH aqueous solution, stirred for 1 hour under reflux and then filtered; after repeating the same ion-exchange operation once more, the product was thoroughly washed, filtered and then dried at 120° C. for 5 hours to obtain Li+-ZSM-5. This product was well mixed with 5.32 g of magnesium acetate (tetrahydrate) with an agate mortar, and calcined at 530° C. for 3 hours in air to obtain a 20 wt% MgO-modified Li+-ZSM-5 catalyst.

EXAMPLE 10-2

Using the MgO-modified Li+-ZSM-5 catalyst prepared in Example 10-1, the catalytic activity test was carried out according to Example 1-2, provided that the reaction condition was as follows: No dilution with nitrogen and SV=200 hr$^{-1}$. The reaction temperature is shown in Table 10 together with the result obtained.

TABLE 10

| Run No. | Reaction temperature (°C.) | Conversion (%) p-Cymene | Conversion (%) Total cymene | Yield (%) Toluene | Yield (%) Propylene | Percent recovery of m-cymene (%) | Purity of propylene (%) |
|---|---|---|---|---|---|---|---|
| 1 | 350 | 33.0 | 12.7 | 11.9 | 11.7 | 99.0 | 100 |
| 2 | 450 | 85.0 | 31.0 | 30.6 | 30.0 | 97.2 | 97.8 |

EXAMPLE 11

Using diisopropylbenzene (m:p=65.5:34.5; abbreviated to DCM) as a material for reaction and MgO-modified Li+-ZSM-5 (SiO$_2$/Al$_2$O$_3$ molar ratio=34.6) prepared in Example 9-1 as a catalyst, reaction was carried out according to Example 1-2, provided that the reaction condition was as follows: DCM/N$_2$=1/4, SV=776 hr$^{-1}$ and reaction temperature=400° C. and 500° C. The result obtained is shown in Table 11.

TABLE 9

| Run No. | N$_2$/CYM (molar ratio) | SV (hr$^{-1}$) | p-Cymene | Total cymene | Toluene | Propylene | Percent recovery of m-cymene (%) | Purity of propylene (%) |
|---|---|---|---|---|---|---|---|---|
| 1 | 3.3 | 874 | 41.0 | 19.3 | 18.2 | 17.7 | 96.5 | 98.7 |
| 2 | 0 | 200 | 49.9 | 20.4 | 19.4 | 18.4 | 95.3 | 94.9 |

REFERENCE EXAMPLE 6

Synthesis of ZSM-5

ZSM-5 was synthesized in the same manner as in Reference Example 3 except that the amount of Al$_2$(SO$_4$)$_3$.17H$_2$O was changed to 29.2 g and the number of agitations was 500 to 550 rpm, provided that, just before shifting to the hydrothermal synthesis, the pH of the mixed liquor was adjusted to 9.55 with addition of an aqueous NaOH solution. The pH just after the hydrothermal synthesis was 12.3. In the same manner as in Reference Example 3, washing with water, drying and then calcination were applied to obtain a white ZSM-5 crystal. As a result of X-ray diffraction measurement, the degree of crystallinity of this product was as low as about 48%, and the SiO$_2$/Al$_2$O$_3$ molar ratio was 15.2.

EXAMPLE 10-1

Five grams of the calcined ZSM-5 obtained in Reference Example 6 was dispersed in a mixed solution of 100

TABLE 11

| Run No. | Reaction temperature (°C.) | Conversion (%) p-DCM | Conversion (%) Total DCM | Percent retention of m-DCM (%) | Yield (%)* Cumene | Yield (%)* Benzene | Yield (%)* Propylene | Purity of propylene (%) |
|---|---|---|---|---|---|---|---|---|
| 1 | 400 | 21.5 | 16.0 | 97.4 | 5.1 | 10.0 | 23.3 | 96.3 |
| 2 | 500 | 43.0 | 31.0 | 93.5 | 3.5 | 24.7 | 47.1 | 91.0 |

*Yield based on the total DCM.

EXAMPLE 12

Two types of ZSM-5 having an SiO$_2$/Al$_2$O$_3$ molar ratio of 84 and 254.4, respectively were synthesized in the same manner as in Reference Example 3 except that the amount of aluminum sulfate charged was changed. Each of them was ion-exchanged with aqueous ammonia and dried at 120° C. for 10 hours to prepare NH$_4$+-ZSM-5. This product was further ion-exchanged twice with a 0.1N-LiCl/0.1N-LiOH aqueous solution for one hour under reflux, and Mg(OAc)$_2$ impregnation/support were applied, followed by calcination at 500° C. for 3 hours. Thus, a 20 wt% MgO-modified Li+-ZSM-5 catalyst was prepared.

Using the catalyst thus prepared, dealkylation of a mixed tert-butyltoluene (m:p=65:35) was carried out according to Example 1-2, provided that the reaction condition was as follows: No dilution with nitrogen, SV=200 hr$^{-1}$ and reaction temperature=450° C. The result obtained is shown in Table 12.

TABLE 12

| Run No. | Si$_2$O/Al$_2$O$_3$ (molar ratio) | Conversion (%) p-Isomer | Yield (%) To-tal | Yield (%) Tol-uene | Yield (%) Iso-buty-lene | Percent recovery of m-isomer (%) | Purity of iso-butylene (%) |
|---|---|---|---|---|---|---|---|
| 1 | 84 | 27.1 | 10.8 | 9.4 | 9.0 | 98.0 | 95.5 |
| 2 | 254.4 | 24.1 | 9.1 | 8.4 | 8.2 | 99.0 | 93.8 |

EXAMPLE 13

The following ZSM type zeolites are prepared based on the methods of the patent specifications as described below.

| ZSM type zeolite | Preparation method |
|---|---|
| ZSM-11 | Japanese Patent Publication No. 23280/1978 |
| ZSM-12 | Japanese Patent Publication No. 16079/1977 |
| ZSM-23 | Japanese Patent Application (OPI) No. 149900/1976 |
| ZSM-35 | Japanese Patent Application (OPI) No. 144500/1978 |
| ZSM-38 | U.S. Pat. No. 4,046,859 |
| ZSM-48 | Japanese Patent Application (OPI) No. 133223/1981 |

These ZSM type zeolites ae treated in the following manner.

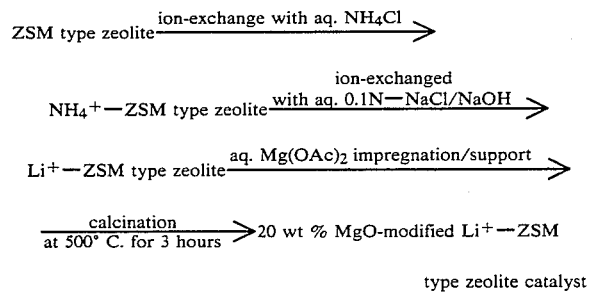

Using each of the catalysts thus obtained, dealkylation of cymene is carried out according to Example 5-2. As the result, only the p-isomer is selectively reacted, whereby a high percent recovery of the m-isomer and a high purity of propylene are attained.

EXAMPLE 14

The ZSM-5 (SiO$_2$/Al$_2$O$_3$=42) as obtained in Reference Example 3 is ion-exchanged with the Li ion according to Example 1-1 and impregnated with an aqueous solution of a compound containing each of the elements as described below (mainly a nitrate, chloride or oxyacid ammonium salt thereof), followed by concentration. Thereafter, calcination is carried out in an air stream at 500° C. for 3 hours to prepare a catalyst in which about 20 wt% of the respective element supported in the oxide form.

| Supporting element | Group |
|---|---|
| La | lanthanum |
| Ba | IIa |
| Zn | IIb |
| Ga | IIIa |
| Pb | IVa |
| P | Va |
| Te | VIa |
| Mo | VIb |
| Mn | VIIb |

Using the thus prepared Li+-ZSM-5 catalysts, dealkylation of cymene is carried out according to Example 5-2. As the result, only the p-isomer is selectively reacted, whereby a high percent recovery of the m-isomer and a high purity of propylene are attained.

While the invention has been described in detail and with reference to specific embodiments thereof, it will be apparent to one skilled in the art that various changes and modifications can be made therein without departing from the spirit and scope thereof.

What is claimed is:

1. A method for selective dealkylation of 1,4-dialkylbenzenes comprising selectively dealkylating a 1,4-dialkylbenzene in a dialkylbenzene mixture using as a catalyst crystalline zeolite having a silica/alumina ratio of at least 12 and a constrained index of 1 to 12 which is modified with an oxide of a metal or metalloid, said crystalline zeolite being one ion-exchanged with a lithium ion.

2. A method as described in claim 1, wherein at least one alkyl gorup of the 1,4-dialkylbenzene is a secondary and/or tertiary alkyl group having 3 to 12 carbon atoms.

3. A method as described in claim 1, wherein the 1,4-dialkylbenzene is 1-isopropyl-4-methylbenzene, 1,4-diisopropylbenzene, 1-sec-butyl-4-methylbenzene or 1-tert-butyl-4-methylbenzene.

4. A method as described in claim 1, wherein the crystalline zeolite is ZSM-5, ZSM-11, ZSM-12, ZSM-23, ZSM-35 or ZSM-48.

5. A method as described in claim 1, wherein the oxide of a metal or metalloid modifying the crystalline zeolite is an oxide of at least one element belonging to the lanthanum group, Group IIa, Group IIb, Group IIIa, Group IVa, Group Va, Group VIa, Group VIb and Group VIIb of the periodic table.

6. A method as described in claim 5, wherein the oxide of a metal or metalloid modifying crystalline zeolite is an oxide of at least one element selected from the group consisting of lanthanum, cerium neodymium, barium, magnesium, strontium, zinc, cadmium, gallium, indium, germanium, tin, lead, phosphorus, tellurium, chromium, molybdenum, tungsten, manganese and rhenium.

7. A method as described in claim 1, wherein the crystalline zeolite is ZSM-5 and the modifying metal is magnesium.

* * * * *